United States Patent [19]

Slonina, deceased et al.

[11] Patent Number: 5,147,321

[45] Date of Patent: Sep. 15, 1992

[54] ROTATIONALLY OPERATED DEVICE FOR ATRAUMATIC ACCESS TO THE BLOOD CIRCUIT

[75] Inventors: Jean-Pierre Slonina, deceased, late of Le Vesinet, by Marie-Noëlle Slonina, Caroline Slonina, Frederic A. Slonina, Aurélie M. Slonina, legal representatives; Sylvie Hamann, Levallois, both of France

[73] Assignee: Biomasys, France

[21] Appl. No.: 301,756

[22] PCT Filed: Jun. 2, 1987

[86] PCT No.: PCT/FR87/00191

§ 371 Date: Jan. 19, 1989

§ 102(e) Date: Jan. 19, 1989

[87] PCT Pub. No.: WO87/07509

PCT Pub. Date: Dec. 17, 1987

[30] Foreign Application Priority Data

Jun. 3, 1986 [FR] France ................. 86 07984

[51] Int. Cl.⁵ ............................................. A61M 5/00
[52] U.S. Cl. .................................. 604/175; 604/43; 604/891.1
[58] Field of Search ............... 604/175, 43, 51, 52, 604/236, 891, 905

[56] References Cited

U.S. PATENT DOCUMENTS

| | | | |
|---|---|---|---|
| 4,092,983 | 6/1978 | Silvenko | 604/175 |
| 4,108,173 | 8/1978 | Silvenko et al. | 604/175 |
| 4,654,033 | 3/1987 | Lapeyre et al. | 604/175 |
| 4,804,369 | 2/1989 | Lapeyre et al. | 604/175 |

Primary Examiner—C. Fred Rosenbaum
Assistant Examiner—C. Maglione
Attorney, Agent, or Firm—Marshall & Melhorn

[57] ABSTRACT

An apparatus for atraumatic access to the blood circuit includes a central tubular section connected to two lateral tubular sections. The central section includes a removable head having a blood taking and blood reinjection line, and a pair for obturating the blood flow, which may be activated by a rotation of the removable head through 90°. The two lateral sections are connected to a vein or artery, forming a shunt. A recess in the closure makes it possible to clean and rinse the interior of the access device. The device makes it possible to treat, as often as necessary, an extra-corporal circulation of a patient's blood.

13 Claims, 4 Drawing Sheets

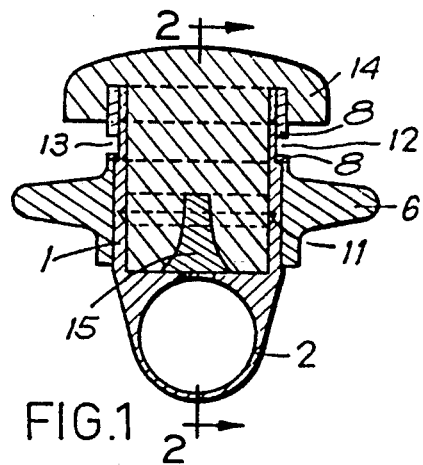
FIG.1
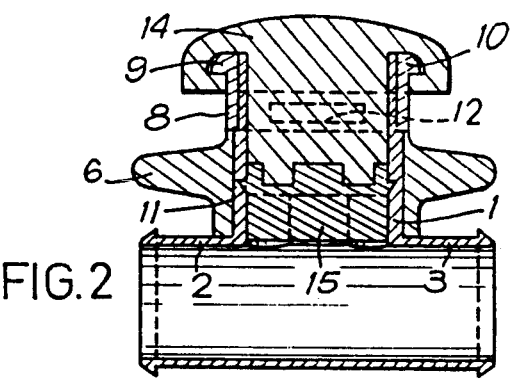
FIG.2
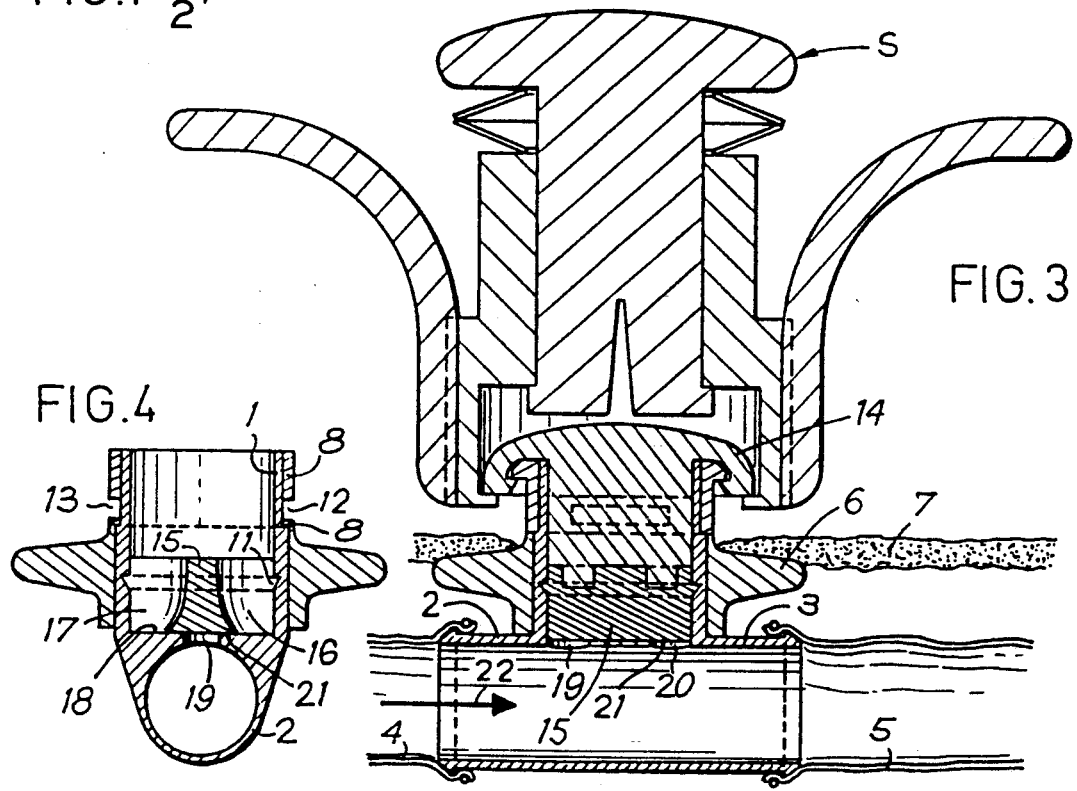
FIG.3
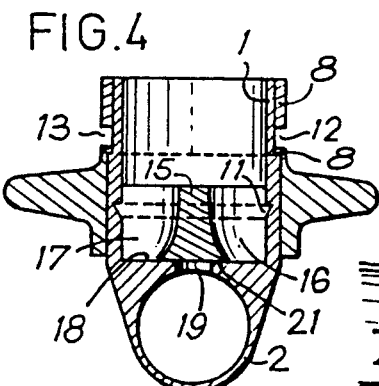
FIG.4
FIG.5
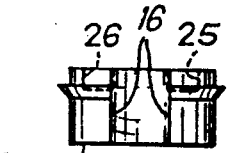
FIG.6
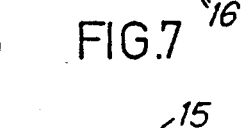
FIG.7
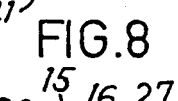
FIG.8
FIG.9
FIG.10
FIG.11

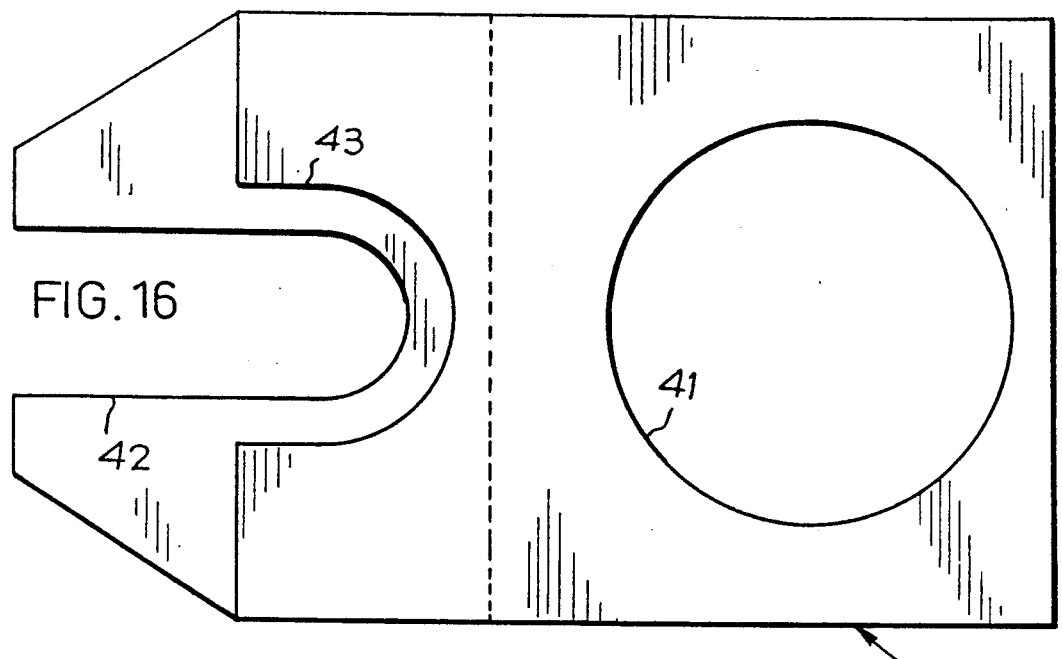
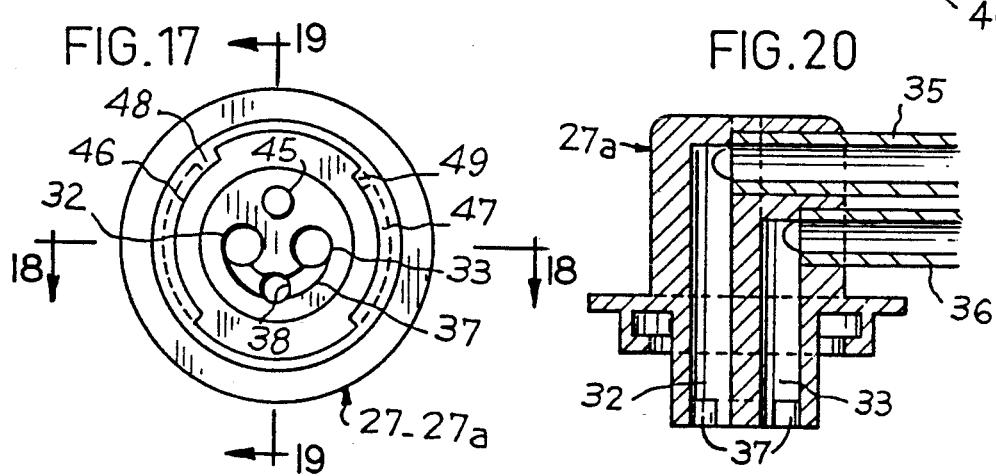
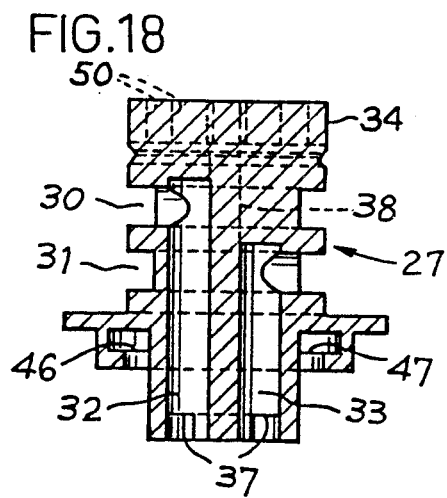
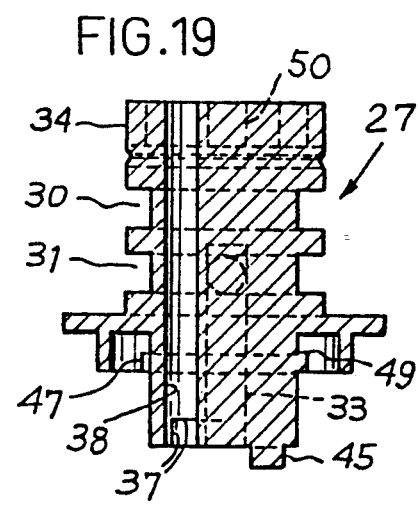

ROTATIONALLY OPERATED DEVICE FOR ATRAUMATIC ACCESS TO THE BLOOD CIRCUIT

BACKGROUND OF THE INVENTION

The present invention relates to a device for atraumatic access to the blood circuit. More particularly, the device comprises an implantable device for percutaneous removal of blood and a mechanism for controlling the flow of blood. The device makes it possible to treat, as often as necessary, an extra-corporal circulation of the blood, for example by an apparatus intended to compensate poor functioning of the kidneys.

Several devices for atraumatic access to the blood circuit are already known and in use, including devices similar to the present invention, having a rigid, biologically compatible, percutaneous body. For example, the prior art discloses devices like the present invention, having a central tubular segment which intersects and connects with the midpoint of another tubular segment, thereby bisecting the other tubular segment into two lateral segments.

The two lateral segments are each connected to an artificial line which is compatible with blood, and capable of being sutured onto an artery or a vein so as to form an arterio-venous shunt constantly traversed by a flow of blood.

The central segment of the T, which passes through the skin of the patient, comprises one or more obturation parts and a means for attaching a removable taking head. The removable head is typically connected to the circuit outside of the patient's body, and is capable of connecting at least one taking line and one reinjection line within the removable head with an internal blood circuit.

Like the present invention, previously known devices have shown blood taking and reinjection lines borne by a removable head and positioned so that an arterio-venous shunt with an internal blood circuit is achieved. The shunt is achieved either through an obturation part contained within the central segment, which passes through the skin, or by a passage in the axial direction through an obturation part and then through taking and reinjection lines.

One object of the present invention is to provide a device having taking and reinjection lines borne by a removable head which may be connected to an arterio-venous shunt by a simultaneous rotation of a removable head and an obturation part.

The atraumatic access devices disclosed by the prior art suffer from one or more of the following principal drawbacks:

Difficulty in applying disinfectant to complex obturation parts during cleaning procedures;

Low blood flow rates;

Complex methods and complicated tools needed for connecting and disconnecting the removable head, so that the patient is normally incapable of utilizing the device correctly with one hand;

Poor external bonding between the skin and the central segment of the device, creating a risk of microbial penetration;

Considerable mechanical stress placed upon the elastomer parts.

SUMMARY OF THE INVENTION

The present invention relates to a device for atraumatic access to the blood circuit. More particularly, the device comprises an implantable device for percutaneous removal of blood and a mechanism for controlling the flow of blood. The device makes it possible to treat, as often as is necessary, an extra-corporal circulation of the blood, for example by an apparatus intended to compensate poor functioning of the kidneys.

The present invention is extremely easy to use, the patient being able to operate it easily with one hand. The design of the present invention is conducive to maintaining asepsis, partly because the implanted device comprises only one mobile part, made of elastomer which is very easy to clean. Asepsis is further promoted because of a circuit which enables disinfection and rinsing so as to eliminate the risk of contamination by microbes contained in the air. In addition, because of the simplicity of the removable head and of the stopper, it is possible to make these parts consumable equipment.

There is minimal mechanical stress applied to the elastomer parts during operation of the present invention. In addition, there is a relatively high blood flow rate due to larger passage sections.

The present invention includes a principal, tubular, metallic, biocompatible body having two intersecting tubular segments, wherein a distal end of the central segment intersects and connects with the midpoint of the other tubular segment, thereby bisecting the other tubular segment into two lateral segments. The two lateral segments are then connected to a vein or artery to form a shunt.

The central segment passes through the skin and is provided with a porous carbon flange which makes a good bond with the skin. Because porous carbon is used for the flange material, there is a good bond between the skin and the body of the device.

A closure is located within the central segment. The closure is made of elastomer and provided with a small flange which is insertable into an inner circular groove in the central segment. The small flange and groove serve to axially position the closure so that the lower face of the closure seats against the inside of the lower face of the central segment, yet still allows rotation of the part.

The closure comprises two passageways oriented so that the plane of their axes is substantially parallel to its axis of rotation. These holes connect with the arterio-venous shunt when they are placed above access openings to the lateral segments. The holes may be isolated from the lateral segments in sufficiently tight manner by rotating the obturation part 90°. In this closed position, the closure open onto a planar face which is an integral part of the central segment and cooperates perfectly with the lower face of the closure.

The removable head includes a cylindrical part which is insertable into the central segment and includes blood taking and reinjection lines.

A face is located at one end of the removable head for elastically abutting the top of the closure, which is also made of elastomer, thereby creating a seal between the holes of the closure and the lines of the removable head.

The removable head is connected to the closure so that rotation of the removable head will in turn rotate the closure. This connection may be accomplished through the extension of the blood taking and reinjection lines or any other means.

The invention is a device for atraumatic access to the blood circuit, of the type comprising a tubular, metallic, biocompatible part wherein two tubular lateral segments are inserted in a subcutaneous arterio-venous shunt. The central tubular segment includes a flange for biological attachment to the skin, preferably made of porous carbon. The invention projects slightly from the surface of the skin, possesses an closure and is adapted to receive and to fix a removable blood taking and reinjection head. When inserting the removable head into the central segment and until contact with the closure occurs, the taking and reinjection lines of the head are necessarily aligned with a corresponding passageway in the closure. When contact between the reinjection head and the closure occurs, the passageways are obturated by the lower sealing face of the central segment, which also serves as support for the lower face of the closure. The execution of an angular movement of about 90° by the removable head about the axis of the central segment causes the closure to experience the same movement due to a coupling means. This rotation places the holes of the closure in communication with the flow of blood of the arterio-venous shunt either directly or via the holes made in the lower face of the central segment. The blood reinjection orifice is always correctly located downstream of the taking orifice.

The means for fixing the removable head on the top of the central segment of the T, above the level of the skin, makes it possible:

to rotate the removable head 90° while maintaining the same axial position;

to lock the removable head in position following the rotation;

to prevent rotation of the closure unless the initial angular position of the removable head with respect to the central segment is correct; and to prevent reversal of the taking and reinjection lines of the removable head with respect to the direction of the flow of blood of the arterio-venous shunt.

Means for locking the removable head is provided by two partially circumferential outer flanges, diametrically opposite and adapted to engage beneath two complementary and cooperating partially circumferential outer flanges borne by the top of the central segment.

The thickness of the flanges is such that rotation of the closure is impossible if the portions of flange of the removable head are not driven between the cooperating flanges of the central segment of the T. Because the flanges are disymmetrical, reversal of the taking and reinjection lines is impossible. Portions of the flanges are provided with a stop and excess thickness section for locking, as will be explained below.

The removable head possesses a rod which is slidable in a cylindrical hole parallel to the axis of the removable head, for obturating a recess located in the lower face of the head and connecting the blood taking and reinjection lines. Because of this recess, cleaning and rinsing with a bactericidal product is possible before recirculation of the blood, so that any bacteria existing in the central segment may be eliminated. After rinsing, the sliding rod is lowered so that the two blood flows will again be isolated. The closure may then be rotated through 90°.

Because of the necessity to rotate the removable head through 90°, it may be equipped with sufficiently supple and long outside connecting lines. Alternatively, the head may be connected to a nonrotating part bearing the outside lines and connected to two circular grooves in the rotating part of the head, each groove communicating with one of the lines of the head.

A stopper may be placed in the central segment after use. The stopper conforms to the shape of the interior cavities of the closure in order to prevent stagnation of fluid. Due to the dissymmetry of the flanges, there is only one position in which the stopper may be inserted into the cavity. Thus, the stopper, which also may be made of elastomer, is prevented from rotating within the cavity due to its shape. The stopper may be removed using a special tool.

The patient possesses a stabilizing tool for preventing rotation of the central segment during rotation of the removable head. The stabilizing tool may be maintained by the patient's index finger while rotation is achieved using the thumb and second finger. Since one hand is sufficient for operation, the patient may carry out this operation himself.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 1 is a sectional view of an blood circuit access device in accordance with the invention, taken through the axis of the lateral segments and showing the stopper in place;

FIG. 2 is a sectional view taken along line 2—2 of FIG. 1;

FIG. 3 is the sectional view illustrated in FIG. 2, additionally showing a device for removing the stopper and the two connecting tubes of the arterio-venous shunt;

FIG. 4 is the sectional view illustrated in FIG. 1 with the stopper removed;

FIG. 5 is a top view of the access device illustrated in FIGS. 1 through 4;

FIG. 6 is a top view of a first embodiment of the closure;

FIG. 7 is a sectional view taken along line 7—7 of FIG. 6;

FIG. 8 is a side view of the closure illustrated in FIG. 6;

FIG. 9 is a top view of a second embodiment of the closure;

FIG. 10 is a sectional view taken along line 10—10 of FIG. 9;

FIG. 11 is a side view of the closure illustrated in FIG. 9;

FIG. 16 is a top view of the stabilizing tool illustrated in FIG. 14;

FIG. 17 is a bottom view of the removable head illustrated in FIG. 12, 13, 14, and 15;

FIG. 18 is a sectional view taken along line 18—18 of FIG. 17;

FIG. 19 is a sectional view taken along line 19—19 of FIG. 17.

FIG. 20 is a sectional view of a removable head possessing only the rotating part;

DETAILED DESCRIPTION OF THE PREFERRED EMBODIMENT

Figure 12:
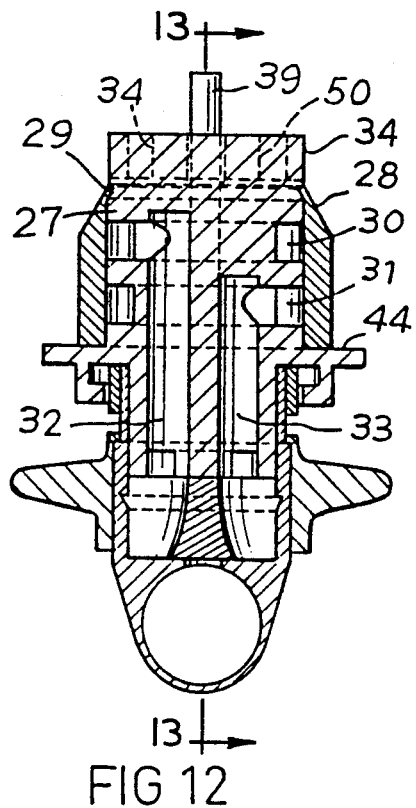
FIG. 12 is a sectional view of an access device taken through the axis of the lateral segments, showing the removable head in place but not locked.
Figure 13:
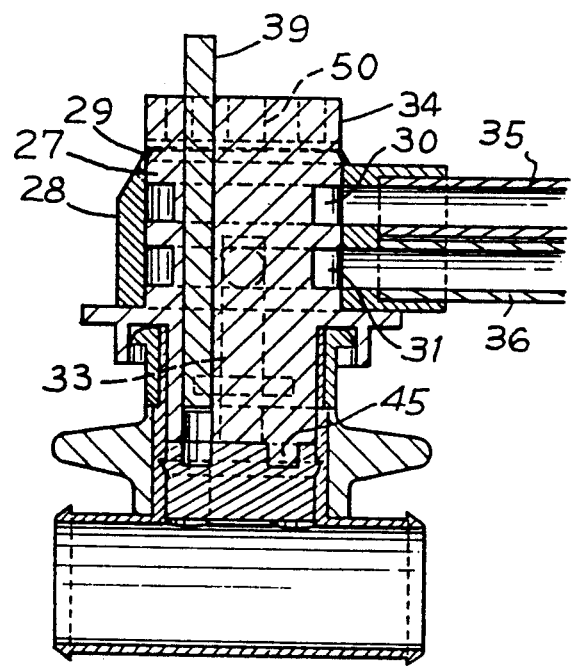
FIG. 13 is a sectional view taken along line 13—13 of the access device illustrated in FIG. 12 and showing outside lines for transport of the blood.

As shown in FIGS. 1 and 2, the blood circuit access devices of the present invention consist of a central tubular segment 1 adapted to communicate with two laterally extending tubular segments 2 and 3. The central segment 1 is typically formed of a metallic and biocompatible material such as, for example, titanium stainless steel, or chromium-cobalt alloy. The distal ends of the segments 2 and 3 may be provided with outside steps, illustrated in FIG. 3, used for attachment to respective connecting tubes 4 and 5 of the arterio-venous shunt. The connecting tubes 4 and 5 are typically formed of a haemocompatible material such as, for example, dacron, for connection with an artery or vein, forming a shunt.

A radially extending flanged portion 6, typically formed of porous carbon, is adapted to surround the tubular segment and provides a solid germ-free attachment with the skin 7 of a patient, as shown in FIG. 3.

A cylindrical sleeve 8 is disposed in surrounding relation on the upper portion of the central segment 1. The sleeve 8 is typically attached by gluing or welding after introduction and gluing of the flanged portion 6. The sleeve 8 includes two outwardly extending flanged portions 9 and 10, as clearly illustrated in FIGS. 2 and 5.

An inner circular groove 11 is formed on the inner surface of the central segment 1 for axially positioning a closure 15. The closure 15 is a typically a valve which includes two outer passageways 16 and 17 for directing blood flow, and a lower face 21 for obturating or preventing blood flow. Two flat portions 12 and 13 on the outer surface of the central segment 1, as illustrated in FIGS. 1, 2, 4 and 5, are adapted to receive a stabilizing tool 40, of the type illustrated in FIGS. 14 and 16, employed to militate against rotation of the segments 1, 2, and 3 during rotation of an associated removable head 27, as will be discussed hereinbelow.

A stopper 14, as illustrated in FIGS. 1, 2 and 3, is formed to extend into each of the passageways 16, 17, 25, and 26 of the closure 15. The stopper 14 and the closure 15 are preferably made of biocompatible elastomer matter such as, for example, polyurethane. A circular flange on the closure 15 is adapted to penetrate into the inner circular groove 11. The use of elastomer provides for suitable sealing properties and allows for less precise parts to be employed.

The stopper 14 may lose some of its efficiency, and therefore, not completely penetrate into the closure 15. Consequently, the stopper 14 could possibly rotate relative to the central segment 1. However, in such a case the stopper 14 would lock on the circumferential flange portions 9 and 10.

The closure 15, on losing some of its efficiency, can be maintained in place by a metal or plastic snap ring.

FIG. 3 illustrates a stopper stripping or removal device generally indicated at S, which may be utilized to prevent undesired forces on the skin since the forces used to operate the device will act to annul one another. The device S may be operated by positioning the index finger and second finger of the patient beneath associated finger supports on the device and thence exerting a simultaneous force with the patient's thumb.

Figure 26:
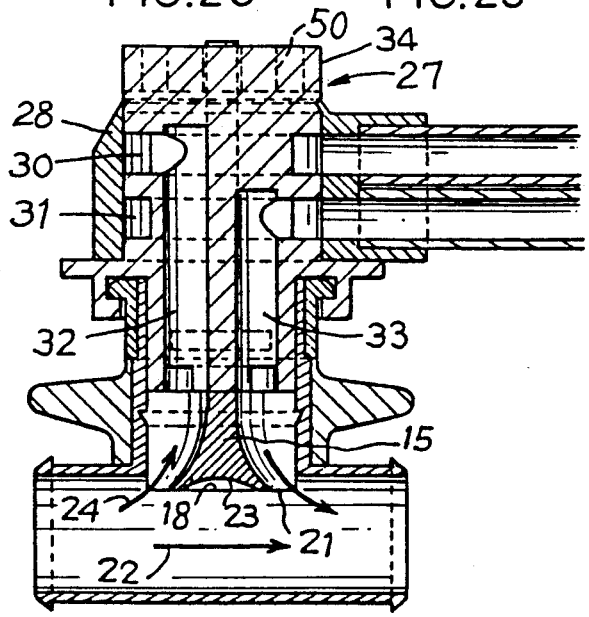
FIG. 26 is a sectional view of an access device showing the closure of FIGS. 9, 10 and 11.

It will be noted from an examination of FIGS. 3 and 5, that two apertures 19 and 20 are formed to provide communication between the central segment 1 and the two lateral segments 2 and 3. After the stopper has been removed, as illustrated in FIG. 4, the closure 15 is in closed position. In the closed position, the passageways 16 and 17 of the closure 15 are closed by a face 18, which is located at the bottom of the central segment 1. In addition, the two holes 19 and 20 for access to the arterio-venous shunt are obturated by the lower face 21 of the closure 15. The face 21 and the cooperating face 18 of the device may, according to the invention, be located at several positions with respect to the top of the bore of the lateral segments 2 and 3, for example, in FIGS. 1 to 4, it lies slightly above the top of the bore of the lateral segments 2 and 3, with the result that there is a very thin wall to pass through by means of the holes 19 and 20. However, in FIGS. 15 and 26, the location is below the top of the bore of the lateral segments 2 and 3. The holes 19 and 20 in the latter case become unnecessary since part 15 and its passageways 16 and 17 plunge directly into the flow of blood 22 when in operative position.

Figure 15:
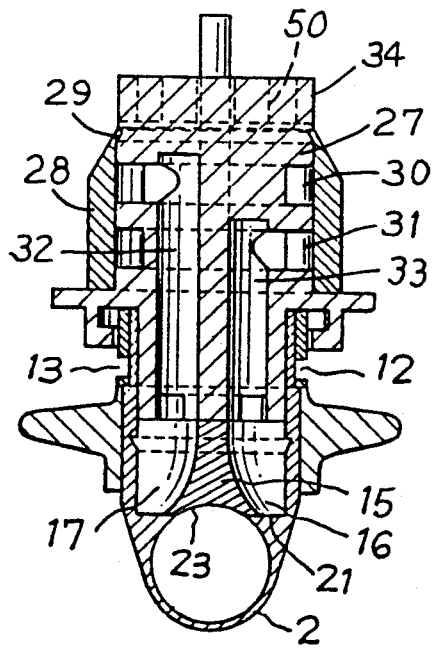
FIG. 15 is a sectional view of an access device similar to FIG. 12 showing the second embodiment of the closure illustrated in FIGS. 9, 10, and 11.

Also, in the latter case, the lower face 21 of the closure 15 has a concave section 23 corresponding to the curvature of the segments 2 and 3. Consequently, when the closure 15 illustrated in FIGS. 9, 10, 11, and 15 is in the closed position as illustrated in FIG. 15, preventing a flow of blood to the passageways 16 and 17, the shape of the bore is constant through the lateral segments 2 and 3, so that there is no disturbance caused to the patient's blood flow.

An access apparatus with the face 21 below the top of the bores of the segments 2 and 3 is necessary only if the flow of blood 22 is too weak and there is consequently a danger that part of the reinjection or outlet flow might mix with the blood inlet flow 24.

Two different embodiments of the closure 15 are illustrated in FIGS. 6 to 8 and 9 to 11, respectively. The two types differ only by the structure of the lower faces thereof. In each of the two embodiments, the passageways 16 and 17 for taking and reinjection of blood from a patient have an inclined profile in order to promote reinjection of the blood in the direction of flow 22.

The closure 15 is formed with cavities or blind holes 25 and 26 for effecting rotation by the removable head 27. The cavities 25 and 26 do not limit the invention as there are numerous ways in which the closure 15 could be rotated. For example, rotation could be accomplished by a slot, for example, formed in the upper surface of the closure 15 to receive a screwdriver.

The rotatable removable head 27 is illustrated in FIGS. 12, 13, 14, 15, 18, 19, 20, 21, 22, and 26. The removable head 27 includes an annulus 34 having a knurled outer periphery 50. A non-rotating sleeve 28 is axially positioned and attached to the rotating removable head 27 by a step 29 formed at the outermost end thereof. It is advantageous, although not necessary, that the sleeve 28 have good elasticity. Numerous plastics materials, such as Delrin, Lexan, polyurethane, for example, are suitable for the non-rotating sleeve 28.

The body of the removable head 27 typically includes two axially spaced apart circular grooves 30 and 31, a blood inlet passageway 32, and a blood reinjection or outlet passageway 33, as illustrated in FIGS. 12, 13, 14, 15, 18, 19, 21, and 26. The grooves 30 and 31 communicate with the inlet passageway 32 and the reinjection or outlet passageway 33, respectively.

A grooved or knurled portion on the annulus 34 is provided to facilitate rotation by the fingers of an operator.

FIG. 20 illustrates another embodiment of removable head 27a which is directly connected to conduits 35 and 36, which communicate with passageways 32 and 33, respectively.

FIG. 17 illustrates the bottom of the removable heads 27 or 27a showing the portion adapted to be inserted into the central segment 1 of the closure 15, slightly compressing the latter axially.

A recess 37 on the lower face of the removable head 27 connects passageways 32 and 33. A cylindrical hole 38 is located to extend parallel to the axis of the head 27 and communicates with the recess 37. The hole 38 is adapted to receive a sliding rod 39, illustrated in FIGS. 12, 13, 14, 15, and 22. The rod 39 is effective to open and close communication between the passageways 32 and 33 via the recess 37, allowing the passageways 32 and 33 to be washed and rinsed and preventing any zones in contact with the blood flow from exposure to the outside air. The communication between the passageway 32 and 33 is eliminated by lowering the rod 39. Then, by rotating the removable head 27 through 90°, the passageways 32 and 33 may be placed in contact with the blood flow. The particular configuration of the recess 37 and of the rod 39, as illustrated, is not absolutely necessary, and is not meant to limit the invention.

Figure 14:
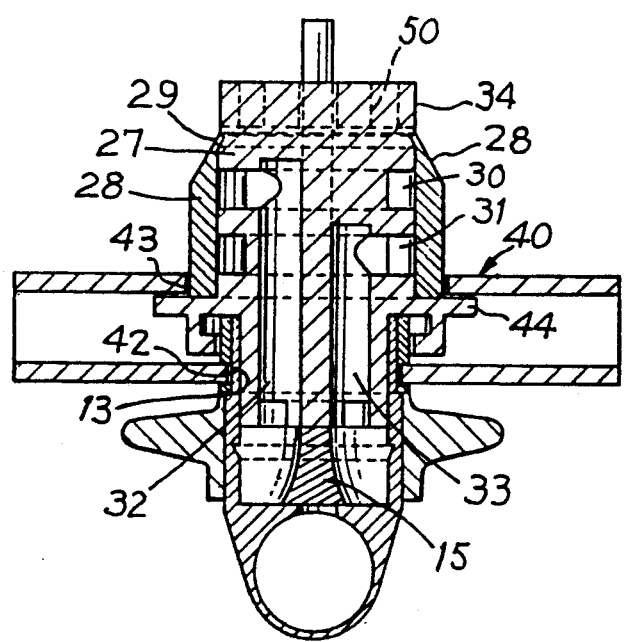
FIG. 14 is a sectional side view of the access device shown in FIG. 12, showing the stabilizing tool in its operable position.

A stabilizing tool 40 to prevent the central segment 1 from rotating during rotation of removable head 27, is illustrated in FIGS. 14 and 16. The stabilizing tool 40 includes a hole or aperture 41 which is adapted to receive the patient's index finger, and a lower slot 42 for engaging the flat portions 12 and 13 of the central segment 1, thereby enabling the stabilizing tool 40 to prevent rotation of the central segment 1. An upper slot 43 is provided to enclose the non-rotating part 28 and prevent lifting of the rotating part 7 by abutting the top of the peripheral flange 44 of the removable head 27.

Internal cleaning and rinsing of the device may be achieved when the removable head 27 is in place but not locked. The stabilizing tool 40 may be used to hold the removable head 27 in this position. When cleaning operations are completed, the patient may press the rod 39 into the hole 26 of the closure 15 in order to block the circular recess 37 and to assist in affecting rotation of the closure 15 via the removable head 27.

As illustrated in FIG. 19, another means for rotating the closure 15 is provided by a catch 45, extending from the lowermost face of the removable head 27. The catch 45 extends into the hole 25 of the closure 15. The catch 45 extends a distance slightly less than the sum of the thicknesses of the circumferential portions of either flanges 9 and 46 or flanges 10 and 47, with the result that the catch 45 can drive the closure 15 in rotation only if the circumferential portions of the respective flanges of the removable head 27 or 27a and the central segment 1 are suitably fitted together.

To access the flow of blood, the patient inserts an index finger into the hole 41 of the stabilizing tool 40 and grips the top of the removable head 27 between the thumb and index finger, and rotates the removable head 27 in a clockwise direction through 90°. After such rotation, the device will be in operable position, as illustrated in FIGS. 21 to 26, and the patient can then withdraw the stabilizing tool 40.

Figure 21:
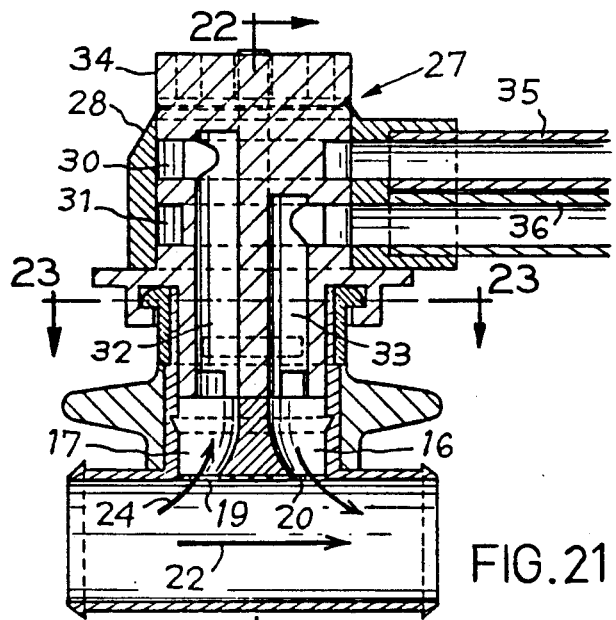
FIG. 21 is a sectional view of an access device showing the removable head in the locked position.
Figure 22:
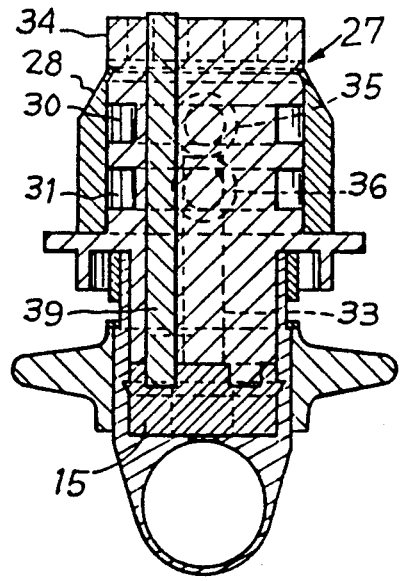
FIG. 22 is a sectional view taken along line 22—22 of FIG. 21.
Figures 23, 24, 25:
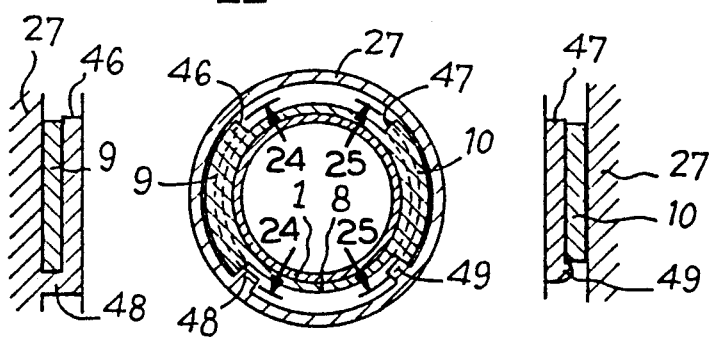
FIG. 23 is a sectional view taken along line 23—23 of FIG. 21.
FIG. 24 is a sectional view taken along arc 24—24 of FIG. 23.
FIG. 25 is a sectional view taken along arc 25—25 of FIG. 23.

As illustrated in FIGS. 21 and 25, during operation of the access device the removed flow of blood 24 first enters the central segment 1 through hole 19 of the central segment. The blood then travels through the passageway 17 of the closure 15, then through the blood inlet passageway 32 and groove 30 of the removable head 27 to the outside blood transport passageway 35, and is transported, for example, to a blood treatment apparatus. After treatment, the blood reinjection flow travels back to the blood circuit access device through the outside blood transport passageway 36, through groove 31 and the blood reinjection passageway 33 of the removable head 27, through the passageway 16 of the closure 15, and exiting the central segment through the hole 20 of the central segment 1, with a blood flow direction which is favorable with respect to the direction of the patient's blood flow 22.

FIGS. 23, 24 and 25 illustrate the respective locking flanges of the central segment 1 and the removable head 27 or 27a, as they appear when the two parts are assembled in operable fashion. The spaced apart circumferential flanges 9 and 10 of the central segment 1 are shown interconnected with the spaced apart circumferential flanges 46 and 47 of the removable head 27 or 27a.

The flanges 46 and 47 of the removable head 27 include a stop 48 and an excess thickness 49 to enable locking of the removable head 27 to the central segment 1, as illustrated in FIGS. 17, 23, 24, 25.

This arrangement is not meant to limit the invention as each flange may possess both an angular stop and an excess thickness section for locking. Similarly, a stop and excess thickness section could be included on the flanges 9 and 10 of the central segment 1.

The removable head 27, which is preferably made of biocompatible plastic such as, for example, PTFE, polyethylene, Delrin, or polycarbonate, is able to withstand the elastic deflection of the flange 47 needed to allow for passage of the excess thickness 49 for locking.

After use, the patient may disable the arterio-venous shunt by inserting the stabilizing tool 40 into the flat portions 12 and 13 and rotating the removable head 27 through 90° in the opposite direction. The rotation effectively causes the holes 19 and 20 of the central segment 1 to be obturated by the closure 15. The patient may then withdraw the stabilizing tool 40, remove the removable head 27, and place a stopper 14 in position.

To improve sterility and increase the convenience of operation by the patient, it is advantageous that the stopper 14 and the removable head 27, 27a be disposable after use. The design of the parts according to the invention makes it possible to obtain these elements very cheaply, thus making them essentially disposable, if desired.

In accordance with the provisions of the patent statutes, the present invention has been described in what is considered to represent its preferred embodiment. However, it should be noted that the invention can be practiced otherwise than as specifically illustrated and described without departing from its spirit or scope.

It is claimed is:

1. A device for atraumatic access to a blood circuit of a patient comprising:
   a tubular conduit insertable into a blood vessel;
   a tubular central segment mounted on and extending from said tubular conduit, said tubular central segment having a bottom wall provided with at least one opening for providing communication between said tubular central segment and said tubular conduit;
   rotatable valve means disposed within said central segment, said rotatable valve means having spaced apart passageways and being rotatable within the central segment between a non-operating position for which the spaced apart passageways are not aligned with the opening and an operative position for which the spaced apart passageways are aligned with the opening, thereby providing selective communication between said tubular conduit communicating with the blood vessel and said central segment; and
   a removable head rotatably disposed within said central segment for selectively rotating said rotatable valve means, said removable head comprising a main body portion having an inlet passageway and an outlet passageway for selective communication with the spaced apart passageways of the valve means.

2. A device according to claim 1, characterized in that the valve means is made of a haemocompatible elastomer material.

3. A device according to claim 2, characterized in that the haemocompatible material is a polyurethane material.

4. A device according to claim 1 wherein said valve means includes a small flange located on its outer periphery and said central segment includes an inner circular groove to retain said small flange, whereby said valve means is positioned axially in said central segment.

5. A device according to claim 1, characterized in that the passageways of the valve means are inclined downwardly and outwardly.

6. A device according to claim 1 wherein said removable head includes two spaced apart circumferential flanges and said central segment includes two complimentary spaced apart circumferential flanges adapted to lockingly engage the flanges of said removable head.

7. A device according to claim 6 wherein the spaced apart circumferential flanges of said removable head are provided with means for limiting rotation of said removable head with respect to said central segment.

8. A device according to claim 1, including at least two flat portions on an outer surface of said central segment.

9. A device according to claim 1, including a stopper conforming substantially to the interior of the tubular central segment and having portions extending into the passageways of the valve means.

10. The device according to claim 1 wherein the spaced apart passageways are axially aligned with said tubular conduit, said tubular conduit being axially inserted into a single blood vessel.

11. The device according to claim 1 wherein said rotatable valve means and said removable head are provided with mutually co-operating locking means providing simultaneous rotation of said rotatable valve means and said rotatable removable head upon rotation of said removable head.

12. A device for atraumatic access to a blood circuit of a patient comprising:
   a tubular conduit insertable into a blood vessel;
   a tubular central segment mounted on and extending from said tubular conduit, said tubular central segment having a bottom wall provided with at least one opening for providing communication between said tubular central segment and said tubular conduit and having an upper part opposite to the bottom part located above the level of the skin of the patient;
   rotatable valve means disposed within said central segment, said rotatable valve means having spaced apart passageways and being rotatable within said central segment between a non-operating position for which the spaced apart passageways are not aligned with the opening and an operative position for which the spaced apart passageways are aligned with the opening, thereby providing selective communication between said tubular conduit communicating with the blood vessel and said central segment; and
   a removable head rotatably disposed within said central segment for selectively rotating said rotatable valve means, said removable head comprising a main body portion having an inlet passageway and an outlet passageway for selective communication with the spaced apart passageways of the valve means and said tubular central segment, the upper part of said tubular central segment including locking means for locking said removable head in the operative position providing communication between the spaced apart passageways of said rotatable valve means and the opening of said tubular central segment.

13. The device according to claim 12 wherein the locking means includes spaced apart external circumferential flanges on said central segment and complementary spaced apart circumferential flanges on said removable head, whereby the flanges on said central segment are adapted to lockingly engage the flanges on said removable head.

* * * * *